United States Patent [19]
Rau et al.

[11] Patent Number: 5,756,438
[45] Date of Patent: May 26, 1998

[54] PERSONAL CLEANSING PRODUCT

[75] Inventors: Allen H. Rau, Cincinnati; Gregory A. Freeman, Waynesville; Hope E. Peters, Cincinnati; Mary A. Schwartz, Hamilton, all of Ohio; Paula J. Thueneman, Taylor Mill, Ky.

[73] Assignee: The Andrew Jergens Company, Cincinnati, Ohio

[21] Appl. No.: 621,965

[22] Filed: Mar. 26, 1996

[51] Int. Cl.$^6$ ............... A61K 7/48; A61K 7/50; C11D 9/48
[52] U.S. Cl. ............ 510/151; 510/153; 510/155; 510/156; 510/474
[58] Field of Search ............... 510/151, 153, 510/155, 156, 474

[56] References Cited

U.S. PATENT DOCUMENTS

| | | | |
|---|---|---|---|
| 4,941,990 | 7/1990 | McLaughlin | 252/121 |
| 5,502,155 | 3/1996 | Weuthen et al. | 252/557 |
| 5,520,840 | 5/1996 | Massaro et al. | 510/151 |
| 5,523,017 | 6/1996 | Moran et al. | 510/151 |
| 5,540,854 | 7/1996 | Fair et al. | 510/152 |
| 5,543,072 | 8/1996 | Fost et al. | 510/151 |

FOREIGN PATENT DOCUMENTS

| | | |
|---|---|---|
| WO 95/30736 | 11/1995 | WIPO. |
| WO 95/30737 | 11/1995 | WIPO. |

OTHER PUBLICATIONS

Abstract, Japanese Patent No. JP 56084798, issued Jul. 10, 1981.

*Primary Examiner*—Paul Lieberman
*Assistant Examiner*—Necholus Ogden
*Attorney, Agent, or Firm*—Oblon, Spivak, McClelland, Maier & Neustadt, P.C.

[57] ABSTRACT

A non-soap cleansing bar is provided which exhibits excellent foaming or lathering characteristics, resistance to cracking on drying, and good textural or "feel" characteristics, which employs a surfactant, filler and waxy binder as essential components. Skin-treatment components, colorants, fragrances and the like may be added as optional components. The bar is produced by a tableting operation that involves melting the waxy binder to obtain excellent wear characteristics and feel.

16 Claims, No Drawings

PERSONAL CLEANSING PRODUCT

BACKGROUND OF THE INVENTION

1. Field of the Invention

This invention pertains to a solid cleansing composition, of the general type and shape of a cleansing bar. Specifically, a tableted, solid cleansing bar is provided with desirable lathering, texture or feel and wear-resistance characteristics.

2. Background of the Prior Art

Cleansing bars containing a high proportion of fillers, such as dextrose, dextrin, oatmeal and the like, as well as other carbohydrate fillers, have been marketed as personal cleansing bars. The cleansing bars have a high degree of filler, to reduce cost, and for bulk. In general, these personal cleansing articles are of the shape and size of familiar bathroom soap bars.

The preparation of a cosmetically acceptable cleansing bar with a high concentration of filler presents several difficulties. It is particularly difficult to provide a product with adequate lathering characteristics. Lathering, or foaming, is a chief requirement of personal cleansing toiletry articles. A high degree of filler present in the composition complicates the ability to produce adequate foaming, generally accomplished by a selection of a particular surfactant or surfactant mix.

Additionally, the personal cleansing articles are designed to be used by rubbing between the palms of the user, into a washcloth or along the skin of the user. Accordingly, an essential aspect of the product is an acceptable "feel" or texture. The higher the proportion of filler in the cleansing bar, the more friction is created, giving rise to a "draggy" feeling in the bar itself.

Another performance parameter that personal cleansing products of this type must meet is aesthetic appearance. A heavy load of filler in commercial products tends to provide an unattractive bar, that cracks or splinters quickly upon use, or that presents a grainy, pebbled surface which is aesthetically unappealing.

Japanese Patent Publication (Kokai) 56-84798, published Jul. 10, 1981 is directed to a soap composition which is recited to contain, by weight, 60–90 percent starch or cellulose. Unlike the non-soap product of the invention, the Kokai is directed to a granular soap which is a compacted powder intended to achieve rapid disintegration, and through disintegration, washing, in contradiction of the invention that is the subject of this application. The dimensions of the product are much smaller than personal cleansing bars, designated as weighing 400–1000 mg, and intended for use as a tablet which disintegrates upon admixture with water.

As noted, other high-filler compositions are known, but none provide a suitable combination of acceptable lathering performance, acceptable feel or texture, and aesthetic properties. Thus, the provision of a personal, non-soap cleansing bar, meeting these identified parameters, continues to be an object of those of skill in the art.

SUMMARY OF THE INVENTION

The above objects, and others explained in more detail below, are met by the provision of a non-soap solid cleansing bar including, as fundamental components, a surfactant component, a waxy binder component, and filler. Exemplary compositions employ a 15–45 percent surfactant component, waxy binders in an amount of 2–20 percent by weight, and a filler in the amount of 40–80 percent by weight. Additionally, emollient oils, skin-conditioning polymers, colorants and fragrance may be added to the inventive subject matter.

The personal cleansing bars of the claimed composition are prepared by a tableting process. The ingredients are mixed together, and heated to melt the waxy binder. Melting of the binder may be achieved by high shear mixing of all components combined, by heating the entire mixture in a jacketed vessel or other heating device or by separate heating of the binder component alone, followed by addition to the other components previously mixed together. The composition is compressed using a tablet press, or briquette-forming apparatus of conventional nature.

The resulting product exhibits exemplary lathering performance, extended wear over multiple uses, and acceptable texture or feel that is neither draggy nor rough, and aesthetically acceptable appearance that resists cracking or disintegration. In preferred embodiments, the bar exhibits a slightly acidic pH, about 5.0–7.0.

DETAILED DESCRIPTION OF THE INVENTION

This invention is described, in detail, below. All percentage values recited are percentage by weight. Percentages, where recited, are approximate, unless indicated to the contrary. It is not the precise numerical value of the percentage recited, unless so indicated, but rather the balance of components selected so as to achieve the performance characteristics outlined above that characterize the claimed invention.

The personal cleansing bar addressed herein can be of any shape and size. It must, however, be of a size acceptable for use by human hands, and is intended for multiple uses. In general, the product will weigh between 3 and 10 ounces and have physical dimensions in excess of several inches in at least one dimension. Specifically, the bar composition of this invention is of a shape and size familiarly known as "facial soap" or "bath soap" sizes.

The personal cleansing bar of this invention relies on proper combination of three fundamental components, a surfactant or surfactant system, filler, and a waxy binder. The waxy binder is melted in preparation of the product, so as to provide excellent aesthetics to the product.

Surfactant:

The surfactant or surfactant system is present in amounts of 15–45 percent. Anionic surfactants are preferred. A particularly preferred surfactant system is sodium cocoyl isethionate (SCI) in combination with sodium dodecyl benzene sulfonate (LAS). These materials are advantageously used in about a 6:1 ratio (SCI:LAS). Other combinations of anionic surfactants perform acceptably. Alternate anionic materials include:

alkyl (C8–18) sulfates (e.g., sodium lauryl sulfate, sodium cetearyl sulfate, sodium lauryl amide methylene sulfate), alkyl (C8–18) ether sulfates (e.g., sodium laureth-x sulfate, x=1 to 12), fatty acid soaps (e.g., sodium stearate, sodium laurate), alkyl (C8–18) sulfonates (e.g., sodium C14–16 olefin sulfonate, sodium cocoglyceryl ether sulfonate, sodium lauryl sulfoacetate), sulfosuccinates (e.g., sodium lauryl sulfosuccinate, disodium laureth sulfosuccinate, disodium cocamido MEA sulfosuccinate), alkyl phosphates (sodium stearyl monophosphate, potassium lauryl phosphate), taurates (e.g., sodium methyl cocoyl taurate), alkyl (C8–18) amino acids, esters, amides and ethers thereof (e.g., acyl glutamates such as sodium cocoyl glutamate, n-lauroyl-β-alanine, alkyl carboxyethylglycinates)

alkyl ether carboxylates (e.g., sodium laureth-13 carboxylate) and sarcosinates (e.g., sodium lauroyl sarcosinate, sodium cocoyl sarcosinate)

linear alkyl benzene sulfonates (e.g. sodium dodecyl, benzene sulfonate).

These materials may be neutralized with sodium, potassium, magnesium, calcium, lithium, or TEA.

Nonionic surfactants such as alcohol ethers (e.g., laureth-3, steareth-6), fatty acid alkanolamides (e.g., cocamide DEA, lauramide MIPA), amine oxides (e.g., lauramine oxide, coamidopropyl amine oxide), sorbitan esters (e.g., sorbitan laurate, sorbitan oleate, sorbitan isostearate, sorbitan palmitate) and alkyl polyglucosides (e.g., decyl polyglucose, lauryl polyglucose) may be used as well, alone or in combination with anionic surfactants. These materials may be used to increase certain performance attributes such as lather or cleaning. Their inclusion will depend on the performance target for the particular product (e.g., high cleaning as opposed to skin care).

Zwitterionic and cationic surfactants may also be used. Acceptable surfactant classes are betaines (e.g., cocamidopropyl betaine), sultaines (e.g., cocamidopropyl hydroxysultaine), quaternary ammonium chlorides (e.g., distearyl dimethylammonium chloride, stearyl trimethyl ammonium chloride) and acylamphoacetates/acylamphopropionates (e.g., sodium lauroamphoacetate, sodium cocoamphopropionate). These surfactants are generally used for their foam building and skin feel improving properties.

Filler:

The inventive product employs about 40–80 percent filler. The function of the filler is to lower the overall cost of the product without imparting any negative characteristics to it. A preferred filler is maltodextrin or a combination of dextrose and maltodextrin. Maltodextrin is a starch hydrozylate. Acid hydrolyzed starches may be used as one method of maintaining a slightly acidic pH. This combination gives good wear rate and aesthetics (low stickiness and the product is resistant to cracking on drying). These materials are used in about a 1:2 ratio (dextrose:maltodextrin). Other carbohydrates, starches and dextrins may be used successfully if they have appropriate binding and solubility characteristics. Other fillers that may be used include inorganic particulate fillers such as talc, kaolin, bentonite clay, carbonate or sulfate salts, as well as sugars, and crystalline polyols such as sorbitols. Fillers that have the ability to adsorb oils are particularly desirable if the particular oils have performance related functionality.

Waxy Binder:

The composition includes about 2–20 percent waxy binder. These materials are needed to optimize the wear rate, feel and cracking characteristics of the product. These materials must be chosen to not dramatically hurt the product's lathering properties. A combination of lauric acid and ethylene glycol distearate works well. An alternative or additional binder may be a wax, such as ceresin wax. Exemplary waxes include paraffin, micro-crystalline waxes, triglyceride waxes, etc. Other fundamentally waxy materials with melting points between 40° C. and 70° C., preferably 40° C.-60° C. also work. Some other potential materials are glycerol esters (e.g., glycerol stearate), fatty acid esters (e.g., sodium cocoyl lactylate), alcohol ethoxylates or propoxylates (e.g., ceteareth-20), polyethylene glycols (e.g., PEG-150), fatty alcohols (e.g., cetyl alcohol, myristyl alcohol) and EO/PO block copolymers (e.g., Poloxamer 188). A preferred combination of surfactant, filler and binder is SCI/LAS (6:1), maltodextrin and wax.

Optional Components:

Some other materials that may be included in the invention are emollient ingredients (e.g., mineral oil, avocado oil, petrolatum, fatty acid esters, silicones), skin conditioning polymers (e.g., cationic cellulose, guar derivatives, polyvinyl alcohol and polyvinyl pyrrolidone), colorants and fragrances. Colorants and fragrances are well known to those of skill in the art.

Processing:

The process used to make these products is important. Generally, bar cleanser products are manufactured by extruding a plastic mass, cutting it into "slugs", and then stamping each piece. The inventive product is produced by mixing the ingredients and then compressing the mixture using a tablet press or briquette-forming machine. It is important that the waxy binder be melted during the forming process. If this material is not melted and allowed to flow around the solid particles during the mixing process, the resulting product will have poor wear characteristics and in-use aesthetics. This is supported by the following Examples. Importantly, this process avoids the need to use significant quantities of stearic acid or sodium stearate, widely used as extrusion plasticizers. These materials may inhibit rapid lather formation.

EXAMPLES

Cleansing bars which contain fillers, particularly carbohydrate fillers are known. However, the lathering and aesthetic performance properties of these items are generally poor. The performance of products made with the inventive technology is surprisingly good. Data which compares three example compositions to three currently marketed filled bars follows. Although preferred compositions employ as little as 24–33 percent surfactant and as much as 63 percent filler, the lather produced is noticeably superior to comparative products that contain as much or more surfactant and much less filler. Also surprisingly, the inventive compositions have good aesthetics: they turn easily in the hand and do not crack.

TABLE 1

EFFECT OF PROCESSING ON BAR PERFORMANCE

FORMULATION

| Ingredient | Percent by weight |
| --- | --- |
| Sodium Cocoyl Isethionate | 32.7 |
| Sodium Dodecylbenzene Sulfonate | 5.0 |
| Maltodextrin | 36.8 |
| Dextrose | 16.0 |
| Ethylene Glycol Distearate | 5.0 |
| Lauric Acid | 4.0 |
| Titanium Dioxide | 0.5 |

PROCESSING

1. Blending all ingredients in a bag (like ribbon blender).
2. High shear blending of all ingredients—no heat.
3. High shear blending of all ingredients—with heat.

| | PROCESS 1 | PROCESS 2 | PROCESS 3 |
| --- | --- | --- | --- |
| Appearance | Brittle, very gritty | Brittle, gritty | Plastic, no grit |
| Durability | Unacceptable | Unacceptable | Acceptable |
| Cracking[1] | 3 | 2 | 1 |
| Easily turns in hand | Unacceptable | Unacceptable | Acceptable |

[1]On a 5-point scale: 5 = many cracks, 1 = very few cracks

TABLE 2

| INGREDIENTS (%) | INVENTION 1 | INVENTION 2 | INVENTION 3 | COMPARISON 1 | COMPARISON 2 | COMPARISON 3 |
|---|---|---|---|---|---|---|
| Surfactants: | | | | | | |
| Sodium Cocoyl Isethionate | 28 | 21 | 28 | 34 | 21 | |
| Disodium Lauryl Sulfosuccinate | | | | | 28 | |
| Sodium Lauryl Sulfoacetate | | | | | | 20–25 |
| Sodium Dodecyl-Benzene Sulfonate | 5 | 3 | 5 | | | |
| TOTAL SURFACTANT | 33 | 24 | 33 | 34 | 48 | 20–25 |
| Fillers: | | | | | | |
| Dextrin | 37 | 44 | 51 | | | 35–40 |
| Dextrose | 16 | 19 | | | | |
| Colloidal Oatmeal | | | | 38 | | |
| Corn Starch | | | | | 10–15 | |
| TOTAL FILLER | 53 | 63 | 51 | 38 | 10–15 | 35–40 |
| Binders: | | | | | | |
| Lauric Acid | 4 | 4 | 4 | | | |
| Ethylene Glycol Distearate | 5 | 5 | 3 | | | |
| Ceresin Wax | | | 2 | | | |
| Cetyl Alcohol | | | | 5–10 | | |
| Cetearyl Alcohol | | | | | 10–15 | |
| Paraffin | | | | | ~10 | Collectively ≅10 |
| Sorbitol | | | | | | |
| Mineral Oil | | | | | | |
| PEG-14M | | | | | | |
| Cellulose Gum | | | | | | |
| TOTAL BINDER | 9 | 9 | 9 | 5–10 | 20–25 | ~10 |
| Other[2] | 5 | 4 | 7 | 18–21 | 11–21 | 25–36 |

[2]Other could include: water, boric acid, urea, lactic acid, dioctyl sodium sulfosuccinate, fragrance, glyceryl stearate, titanium dioxide, octyldodecanol, cyclopentadecanol, lanolin alcohol, bisabolol, sodium lactate, glycerin, PEG-90M, magnesium aluminum silicate, benzaldehyde, potassium sorbate, iodopropynyl butyl carbamate, nopyl acetate, isopentylcyclohexanone, polyoxymethylene urea, camphylcyclohexanol.

TABLE 3

| INGREDIENTS (%) | INVENTION 1 | INVENTION 2 | INVENTION 3 | COMPARISON 1 | COMPARISON 2 | COMPARISON 3 |
|---|---|---|---|---|---|---|
| MOISTURE (LOSS ON DRYING) | <5 | <5 | <5 | ~12 | ~9 | ~12 |
| LATHER EVALUATION:[3,4] | | | | | | |
| Amount | 4 | 3.5 | 4 | 3.5 | 1.5 | 2 |
| Quickness | 4.5 | 4 | 4 | 3.5 | 1.5 | 2 |
| Bubbliness | 4 | 4 | 4 | 3.5 | 2 | 2 |
| Creaminess | 4 | 4 | 4 | 3 | 2.5 | 2 |

[3]This provides an evaluation of the lather performance of cleansing bars. A trained panel uses the bars in a handwash, rating the products on a five-point scale with 5 = very or very much and 1 = little or very little.
[4]Lather Procedure Hold the bar with both hands under running tap water (40° C.+/−1) for five seconds. (Water hardness average 115 ppm). Remove hands from water and rotate the bar 20 half turns. Place the bar in the soap dish then continue to work up later in hands for several seconds. Rinse hands and towel dry. Be consistent in the amount of time lathering each product.

COMPARISON TESTING AMONG EXPERT EVALUATIONS*
PERCENT PREFERENCE FROM A HANDWASH EVALUATION

|  | INVENTION 2 | COMPARISON 1 | INVENTION 2 2 | COMPARISON 2 | INVENTION 3 | COMPARISON |
|---|---|---|---|---|---|---|
| Overall Preference | 100 | 0 | 68 | 17 | 60 | 40 |
| Lather Amount | 100 | 0 | 100 | 0 | 60 | 20 |
| Quick Lathering | 100 | 0 | 100 | 0 | 60 | 0 |
| Bubbly Lather | 80 | 20 | 85 | 0 | 60 | 20 |
| Creamy Lather | 100 | 0 | 67 | 33 | 80 | 20 |
| Bar turns easily in hand | 100 | 0 | 17 | 33 | 40 | 0 |

*% Preference from a paired comparison handwash evaluation. If % preference for invention plus % preference for Comparison does not total 100%, the difference equals % no preference.
Lather Procedure: Hold the bar with both hands under running tap water (40° C./–1) for five seconds. (Water hardness average 115 ppm). Remove hands from water and rotate the bar 20 half turns. Place the bar in the soap dish then continue to work up lather in hands for several seconds. Rinse hands and towel dry. Be consistent in the amount of time lathering each product.
Evaluation Procedure: Evaluate the pair of bars on a 5-point scale for each attribute.
5-point Scale:
Prefer Invention Very Much
Prefer Invention Somewhat
No Preference
Prefer Comparison Somewhat
Prefer Comparison Very Much The inventive subject matter of this application has been described above in both generic terms, and by specific example. The specific identities in examples are not intended as, and should not be construed as, limiting, save where expressly so indicated. Variations within the generic classes identified, including other specific chemical constituents, additives, process conditions and the like will occur to those of ordinary skill in the art, without the exercise of inventive faculty. Such variations remain within the scope of the invention, save as excluded by the claims set forth below.

What is claimed is:

1. A non-soap cleansing bar, having good foaming characteristics and resistance to cracking or drying, comprising:

a) about 15–45 percent of a surfactant comprising at least one anionic surfactant, b) about 40–80 percent filler selected from the group consisting of non-starch carbohydrates, starches, starch hydrolyzates, inorganic particulate fillers and mixtures thereof, and c) about 2–20 percent waxy binder having a melting point of 40° C.–70° C. selected from the group consisting of waxes, glycerol esters, glycol diesters, fatty acid esters, alcohol ethoxylates, alcohol propoxylates, ethylene oxide/propylene oxide block copolymers, fatty acids, and mixtures thereof, wherein the ratio of surfactant to waxy binder is from about 4 to 1 to 2.6 to 1.

2. The cleansing bar of claim 1, wherein said anionic surfactant is selected from the group consisting of acyl isethionates, alkyl sulfates, alkyl ether sulfates, alkyl sulfonates, sulfosuccinates, alkyl phosphates, taurates, alkyl amino acid esters, linear alkyl benzene sulfonates, alkyl ether carboxylates and sarcosinates, said anionic surfactant being neutralized with a neutralizing agent selected from the group consisting of sodium, potassium, magnesium, calcium, lithium or triethanolamine.

3. The cleansing bar of claim 2, wherein said surfactant further includes at least one of a nonionic surfactant, zwitterionic surfactant and cationic surfactant.

4. The composition of claim 1, wherein said surfactant comprises a combination of sodium cocoyl isethionate (SCI) and linear alkyl benzene sulfonate (LAS).

5. The cleansing bar of claim 4, wherein said SCI and LAS is present in a ratio of SCI/LAS of about 6:1.

6. The cleansing bar of claim 1, wherein said filler is comprised of maltodextrin.

7. The cleansing bar of claim 6, wherein said filler also comprises dextrose.

8. The cleansing bar of claim 5, wherein said filler comprises maltodextrin.

9. The cleansing bar of claim 1, wherein said waxy binder comprises a combination of lauric acid and ethylene glycol distearate.

10. The cleansing bar of claim 1, wherein said waxy binder comprises a wax having a melting point of about 40° C.–70° C.

11. The cleansing bar of claim 8, wherein said bar comprises, as a waxy binder a wax having a melting point of about 40° C.–70° C.

12. The cleansing bar of claim 1, wherein said bar further comprises at least one component selected from the group consisting of emollient oils, skin-conditioning polymers, colorants and fragrance.

13. The cleansing bar of claim 12, wherein said emollient is selected from the group consisting of mineral oil, petrolatum, fatty acid esters, silicones and mixtures thereof.

14. The cleansing bar of claim 12, wherein said skin-conditioning polymer is selected from the group consisting of cationic cellulose, guar derivatives, polyvinyl alcohol, polyvinyl pyrolidone and mixtures thereof.

15. A method of making the cleansing bar of claim 1, comprising dry-mixing said surfactant, filler and waxy binder, and compressing the mixture into a bar using a bar-forming apparatus, wherein said waxy binder is melted during the process of forming said bar.

16. The cleansing bar of claim 11, wherein said waxy binder has a melting point of about 40° C.–60° C.

* * * * *